(12) United States Patent
Brain

(10) Patent No.: US 7,506,648 B2
(45) Date of Patent: *Mar. 24, 2009

(54) LARYNGEAL MASK AIRWAY DEVICE

(75) Inventor: Archibald I. J. Brain, Les Bons Villers (BE)

(73) Assignee: The Laryngeal Mask Company Ltd., Victoria, Mahe (SC)

( * ) Notice: Subject to any disclaimer, the term of this patent is extended or adjusted under 35 U.S.C. 154(b) by 27 days.

This patent is subject to a terminal disclaimer.

(21) Appl. No.: 11/193,525

(22) Filed: Jul. 29, 2005

(65) Prior Publication Data

US 2005/0274383 A1 Dec. 15, 2005

Related U.S. Application Data

(62) Division of application No. 09/412,954, filed on Oct. 5, 1999, now Pat. No. 7,156,100.

(30) Foreign Application Priority Data

Oct. 6, 1998 (GB) .................................. 9821771.4

(51) Int. Cl.
*A61M 16/00* (2006.01)
*A61M 25/00* (2006.01)
*A61M 16/04* (2006.01)
*A62B 9/04* (2006.01)

(52) U.S. Cl. ............................ 128/207.15; 128/207.14; 128/200.26; 604/96.01

(58) Field of Classification Search ............ 128/207.14, 128/207.15, 207.16, 200.24, 200.26, 206.26; 604/96.01, 100.01, 102.01, 102.02, 102.03
See application file for complete search history.

(56) References Cited

U.S. PATENT DOCUMENTS

| 2,862,498 A | 12/1958 | Weekes |
| 3,529,596 A | 9/1970 | Garner |
| 3,554,673 A | 1/1971 | Schwartz et al. |

(Continued)

FOREIGN PATENT DOCUMENTS

CA 2067782 6/1999

(Continued)

OTHER PUBLICATIONS

Abdelatti, "A Cuff Pressure Controller for Tracheal Tubes and Laryngeal Mask Airway," Anaesthesia, 1999, vol. 54, pp. 981-986.

(Continued)

*Primary Examiner*—Justine R Yu
*Assistant Examiner*—Clinton Ostrup
(74) *Attorney, Agent, or Firm*—Wilmer Cutler Pickering Hale and Dorr LLP

(57) ABSTRACT

A modified laryngeal mask airway device (LMA-device) is provided with means to improve ease of insertion, reliability of function and higher seal pressure (i.e., cuff pressure ratio). The LMA-device includes an indented section of the airway tube to offer locating means and purchase for the inserting finger, and extended mask aperture bars to increase the effective ventilating area of the mask and reduce the possibility of epiglottis displacement occasioned by mask insertion. The LMA-device further includes a modification of the airway tube angle of attachment to the mask, and provision of a posterior or back-cushion covering the entire posterior surface of the mask.

15 Claims, 4 Drawing Sheets

U.S. PATENT DOCUMENTS

| | | |
|---|---|---|
| 3,683,908 A | 8/1972 | Michael et al. |
| 3,794,036 A | 2/1974 | Carroll |
| 3,931,822 A | 1/1976 | Marici |
| 4,067,329 A | 1/1978 | Winicki et al. |
| 4,104,357 A | 8/1978 | Blair |
| 4,116,201 A | 9/1978 | Shah |
| 4,134,407 A | 1/1979 | Elam |
| 4,159,722 A | 7/1979 | Walker |
| 4,178,938 A | 12/1979 | Au et al. |
| 4,178,940 A | 12/1979 | Au et al. |
| 4,231,365 A | 11/1980 | Scarberry |
| 4,256,099 A | 3/1981 | Dryden |
| 4,285,340 A | 8/1981 | Gezari et al. |
| 4,351,330 A | 9/1982 | Scarberry |
| 4,471,775 A | 9/1984 | Clair et al. |
| 4,501,273 A | 2/1985 | McGinnis |
| 4,509,514 A | 4/1985 | Brain |
| 4,510,273 A | 4/1985 | Miura et al. |
| 4,526,196 A | 7/1985 | Pistillo |
| 4,553,540 A | 11/1985 | Straith |
| 4,583,917 A | 4/1986 | Shah |
| 4,630,606 A | 12/1986 | Weerda et al. |
| 4,689,041 A | 8/1987 | Corday et al. |
| 4,770,170 A | 9/1988 | Sato et al. |
| 4,793,327 A | 12/1988 | Frankel |
| 4,825,862 A | 5/1989 | Sato et al. |
| 4,832,020 A | 5/1989 | Augustine |
| 4,850,349 A | 7/1989 | Farahany |
| 4,856,510 A | 8/1989 | Kowalewski et al. |
| 4,872,483 A | 10/1989 | Shah |
| 4,924,862 A | 5/1990 | Levinson |
| 4,953,547 A | 9/1990 | Poole, Jr. |
| 4,981,470 A | 1/1991 | Bombeck, IV |
| 4,995,388 A | 2/1991 | Brain |
| 5,038,766 A | 8/1991 | Parker |
| 5,042,469 A | 8/1991 | Augustine |
| 5,042,476 A | 8/1991 | Smith |
| 5,203,320 A | 4/1993 | Augustine |
| 5,218,970 A | 6/1993 | Turnbull et al. |
| 5,235,973 A | 8/1993 | Levinson |
| 5,241,956 A | 9/1993 | Brain |
| 5,249,571 A | 10/1993 | Brain |
| 5,273,537 A | 12/1993 | Haskvitz et al. |
| 5,277,178 A | 1/1994 | Dingley et al. |
| 5,282,464 A | 2/1994 | Brain |
| 5,297,547 A | 3/1994 | Brain |
| 5,303,697 A | 4/1994 | Brain |
| 5,305,743 A | 4/1994 | Brain |
| 5,311,861 A | 5/1994 | Miller et al. |
| 5,331,967 A | 7/1994 | Akerson et al. |
| 5,339,805 A | 8/1994 | Parker |
| 5,339,808 A | 8/1994 | Don Michael |
| 5,355,879 A | 10/1994 | Brain |
| 5,361,753 A | 11/1994 | Pothmann et al. |
| 5,391,248 A | 2/1995 | Brain |
| 5,400,771 A | 3/1995 | Pirak et al. |
| 5,421,325 A | 6/1995 | Cinberg et al. |
| 5,452,715 A | 9/1995 | Boussignac et al. |
| 5,459,700 A | 10/1995 | Jacobs |
| 5,487,383 A | 1/1996 | Levinson |
| 5,529,582 A | 6/1996 | Fukuhara |
| 5,546,935 A | 8/1996 | Champeau |
| 5,546,936 A | 8/1996 | Virag et al. |
| 5,551,420 A | 9/1996 | Lurie et al. |
| 5,554,673 A | 9/1996 | Shah |
| 5,569,219 A | 10/1996 | Hakki et al. |
| 5,577,693 A | 11/1996 | Corn |
| 5,582,167 A | 12/1996 | Joseph |
| 5,584,290 A | 12/1996 | Brain |
| 5,599,301 A | 2/1997 | Jacobs et al. |
| 5,623,921 A | 4/1997 | Kinsinger et al. |
| 5,626,151 A | 5/1997 | Linden |
| 5,632,271 A | 5/1997 | Brain |
| RE35,531 E | 6/1997 | Callaghan et al. |
| 5,653,229 A | 8/1997 | Greenberg |
| 5,655,528 A | 8/1997 | Pagan |
| 5,682,880 A | 11/1997 | Brain |
| 5,692,498 A | 12/1997 | Lurie et al. |
| 5,694,929 A | 12/1997 | Christopher |
| 5,711,293 A | 1/1998 | Brain |
| 5,738,094 A | 4/1998 | Hoftman |
| 5,743,254 A | 4/1998 | Parker |
| 5,743,258 A | 4/1998 | Sato et al. |
| 5,746,202 A | 5/1998 | Pagan |
| 5,771,889 A | 6/1998 | Pagan |
| 5,778,872 A | 7/1998 | Fukunaga et al. |
| 5,791,341 A | 8/1998 | Bullard |
| 5,816,240 A | 10/1998 | Komesaroff |
| 5,819,723 A | 10/1998 | Joseph |
| 5,832,916 A | 11/1998 | Lundberg et al. |
| 5,850,832 A | 12/1998 | Chu |
| 5,855,203 A | 1/1999 | Matter |
| 5,856,510 A | 1/1999 | Meng et al. |
| 5,860,418 A | 1/1999 | Lundberg et al. |
| 5,865,176 A | 2/1999 | O'Neil |
| 5,878,745 A | 3/1999 | Brain |
| 5,881,726 A | 3/1999 | Neame |
| 5,893,891 A | 4/1999 | Zahedi et al. |
| 5,896,858 A | 4/1999 | Brain |
| 5,915,383 A | 6/1999 | Pagan |
| 5,924,862 A | 7/1999 | White |
| 5,937,860 A | 8/1999 | Cook |
| 5,957,133 A | 9/1999 | Hart |
| 5,979,445 A | 11/1999 | Neame et al. |
| 5,983,891 A | 11/1999 | Fukunaga |
| 5,983,894 A | 11/1999 | Fukunaga et al. |
| 5,983,896 A | 11/1999 | Fukunaga et al. |
| 5,983,897 A | 11/1999 | Pagan |
| 5,988,167 A | 11/1999 | Kamen |
| 5,996,582 A | 12/1999 | Turnbull |
| 6,003,510 A | 12/1999 | Anunta |
| 6,003,511 A | 12/1999 | Fukunaga et al. |
| 6,003,514 A | 12/1999 | Pagan |
| 6,012,452 A | 1/2000 | Pagan |
| 6,021,779 A | 2/2000 | Pagan |
| 6,050,264 A | 4/2000 | Greenfield |
| 6,062,219 A | 5/2000 | Lurie et al. |
| 6,070,581 A | 6/2000 | Augustine et al. |
| 6,079,409 A | 6/2000 | Brain |
| D429,811 S | 8/2000 | Bermudez et al. |
| 6,095,144 A | 8/2000 | Pagan |
| 6,098,621 A | 8/2000 | Esnouf et al. |
| 6,110,143 A | 8/2000 | Kamen |
| 6,115,257 A | 9/2000 | Laity |
| 6,116,243 A | 9/2000 | Pagan |
| 6,119,695 A | 9/2000 | Augustine et al. |
| 6,131,571 A | 10/2000 | Lampotang et al. |
| 6,149,603 A | 11/2000 | Parker |
| 6,155,257 A | 12/2000 | Lurie et al. |
| 6,213,120 B1 | 4/2001 | Block et al. |
| 6,224,562 B1 | 5/2001 | Lurie et al. |
| 6,234,985 B1 | 5/2001 | Lurie et al. |
| 6,240,922 B1 | 6/2001 | Pagan |
| 6,251,093 B1 | 6/2001 | Valley et al. |
| 6,269,813 B1 | 8/2001 | Fitzgerald et al. |
| 6,315,739 B1 | 11/2001 | Merilainen et al. |
| 6,390,093 B1 | 5/2002 | Mongeon |
| 6,427,686 B2 | 8/2002 | Augustine et al. |
| 6,439,232 B1 | 8/2002 | Brain |
| 6,450,164 B1 | 9/2002 | Banner et al. |
| 6,631,720 B1 | 10/2003 | Brain et al. |
| 6,647,984 B1 | 11/2003 | O'Dea et al. |
| 6,651,666 B1 | 11/2003 | Owens |
| 6,705,318 B1 | 3/2004 | Brain |

| | | | | |
|---|---|---|---|---|
| 6,705,322 | B2 * | 3/2004 | Chang | 128/207.15 |
| 6,761,170 | B2 | 7/2004 | Van Landuyt | |
| 7,004,169 | B2 | 2/2006 | Brain et al. | |
| 7,040,322 | B2 | 5/2006 | Fortuna et al. | |
| 7,051,096 | B1 | 5/2006 | Krawiec et al. | |
| 7,089,943 | B2 * | 8/2006 | Chang | 128/207.15 |
| 7,096,868 | B2 | 8/2006 | Tateo et al. | |
| 7,156,100 | B1 | 1/2007 | Brain et al. | |
| 2003/0051734 | A1 | 3/2003 | Brain | |
| 2003/0131845 | A1 | 7/2003 | Lin | |
| 2005/0178388 | A1 * | 8/2005 | Kuo | 128/207.14 |

FOREIGN PATENT DOCUMENTS

| | | |
|---|---|---|
| CA | 2012750 | 8/1999 |
| EP | 0 294 200 | 12/1988 |
| EP | 0 389 272 | 9/1990 |
| EP | 0 402 872 | 12/1990 |
| EP | 0 580 385 | 5/1996 |
| EP | 0712638 | 5/1996 |
| EP | 0732116 A2 | 9/1996 |
| EP | 0796631 | 9/1997 |
| EP | 0845276 | 6/1998 |
| EP | 0865798 | 9/1998 |
| EP | 0922465 | 6/1999 |
| EP | 1125595 | 8/2001 |
| EP | 1 119 386 B1 | 9/2005 |
| GB | 2111394 | 7/1983 |
| GB | 2205499 | 1/1991 |
| GB | 2298797 A | 9/1996 |
| GB | 2317342 | 3/1998 |
| GB | 2317830 | 4/1998 |
| GB | 2318735 | 5/1998 |
| GB | 2319478 | 5/1998 |
| GB | 2321854 | 8/1998 |
| GB | 2323289 | 9/1998 |
| GB | 2323290 | 9/1998 |
| GB | 2323291 | 9/1998 |
| GB | 2323292 | 9/1998 |
| GB | 2359996 | 9/2001 |
| JP | 10118182 | 5/1998 |
| JP | 10216233 | 8/1998 |
| JP | 10263086 | 10/1998 |
| JP | 10277156 | 10/1998 |
| JP | 10314308 | 12/1998 |
| JP | 10323391 | 12/1998 |
| JP | 10328303 | 12/1998 |
| JP | 11128349 | 5/1999 |
| JP | 11192304 | 7/1999 |
| JP | 11206885 | 8/1999 |
| WO | WO-91/03207 | 3/1991 |
| WO | WO-91/07201 | 5/1991 |
| WO | WO-91/12845 | 9/1991 |
| WO | WO-92/13587 | 8/1992 |
| WO | WO-95/33506 | 12/1995 |
| WO | WO-97/12640 | 4/1997 |
| WO | WO-97/12641 | 4/1997 |
| WO | WO-98/16273 | 4/1998 |
| WO | WO-99/06093 | 2/1999 |
| WO | WO-00/09189 | 2/2000 |
| WO | WO-00/22985 | 4/2000 |
| WO | WO-00/23135 | 4/2000 |
| WO | WO-00/61212 | 10/2000 |

OTHER PUBLICATIONS

Benumof, "Laryngeal Mask Airway and the ASA Difficult Airway Algorithm," Anesthesiology, 1996, vol. 84(3), pp. 686-699.

Bernhard et al., "Adjustment of Intracuff Pressure to Prevent Aspiration," Anesthesiology, 1979, vol. 50(4), pp. 363-366.

Bernhard et al., "Physical Characteristics of and Rates of Nitrous Oxide Diffusion into Tracheal Tube Currs," Anesthesiology, 1978, vol. 48, pp. 413-414.

Brain, "The Laryngeal Mask—A New Concept in Airway Management," Br. J. Anaesth., 1983, vol. 55, pp. 801-805.

Brain, "The Laryngeal Mask Airway—A Possible New Solution to Airway Problems in the Emergency Situation," Archives of Emergency Medicine, 1984, vol. 1, pp. 229-232.

Brain, "The Laryngeal Mask Airway," Anaesthesia, 1985, vol. 40, pp. 356-361.

Brain, "Three Cases of Difficult Intuition Overcome by the Laryngeal Mask Airway," Anaesthesia, 1985, vol. 40, pp. 353-355.

Brain, et al., "A New Laryngeal Mask Prototype," Anaesthesia, 1995, vol. 50, pp. 42-48.

Brimacombe, "The Split Laryngeal Mask Airway," p. 639.

Broderick et al., "The Laryngeal Mask Airway," Anaesthesia, 1989, vol. 44, pp. 238-241.

Burgard, et al., "The Effect of Laryngeal Mask Cuff Pressure on Postoperative Sore Throat Incidence," J. Clinical Anesthesia, 1996, vol. 8, pp. 198-201.

Caplan et al., "Adverse Respiratory Events in Anesthesia: A Closed Claims Analysis", Anesthesiology, vol. 72, pp. 828-833, 1990.

Communication of a notice of opposition, European Patent Office, Feb. 15, 2006 (cover page and pp. 1-4).

Craven, "Prevention of Hospital-Acquired Pneumonia: Measuring Effect in Ounces, Pounds and Tonds," Annals of Interal Medicine, 1995, vol. 122(3), pp. 229-231.

Cuff-Pressure-Control DCR, 2000, LogoMed.

Davies, et al., "Laryngeal Mask Airway and Tracheal Tube Insertion by Unskilled Personnel," The Lancet, vol. 336, pp. 977-979.

DeMello, et al., "The Use of the Laryngeal Mask Airway in Primary Anaesthesia," Anaesth. Corresp., 1990, vol. 45, pp. 793-794.

Doyle et al., "Intraoperative Awareness: A Continuing Clinical Problem," http://doyle.ibme.utoronoto.ca/anesthesia/aware.htm.

Engbers, "Practical Use of 'Diprifusor' Systems," Anaesthesia, 1998, vol. 53(1), pp. 28-34.

Eriksson et al., "Functional Assessment of the Pharynx at Rest and During Swallowing in Partially Paralyzed Humans," Anesthesiology, 1997, vol. 87(5), pp. 1035-1042.

European Patent Office, International Search Report for PCT/GB98/03849 (WO 99/33508), mailed Sep. 4, 1999, 4 pages.

Glen, "The Development of 'Diprifusor': A TCI System for Propofol," Anaesthesia, 1998, vol. 53(1), pp. 13-21.

Gray et al., "Development of the Technology for 'Diprifusor' TCI Systems," Anaesthesia, 1998, vol. 53(1), pp. 22-27.

Heath, "Endotracheal Intubation Through the Laryngeal Mask—Helpful When Laryngoscopy is Difficult or Dangerous," European J. of Anaesthesiology, 1991, vol. 4, pp. 41-45.

Hickev. et al.. "Cardiovascular Response to Insertion of Brain's Laryngeal Mask," Anaesthesia. 1990, vol. 45, pp. 629-633.

"Improving Anaesthesia", Med Pro Monthly, Nov./Dec. 1998, pp. 311-312.

Inomata et al., "Transient Bilateral Vocal Cord Paralysis After Insertion of a Laryngeal Mask Airway," Anesthesiology, 1995, vol. 82, pp. 787-788.

Jacobson et al., "A Study of Intracuff Pressure Measurements, Trends and Behaviours in Patients During Prolonged Period of Tracheal Intubation," Br. J. Anaesth., 1981, vol. 53, pp. 97.

Kambic et al., "Intubation Lesions of the Larynx," Br. J. Anasth. 1978, vol. 50, pp. 587-590.

Laryngeal Mask Publications, 74 pages, Dec. 1998, www.saga.nl/lma/lmapub.htm.

Lindholm, "Prolonged Endotracheal intubation," ACTA Anaesthesiologica Scandinavica, 1969, vol. 33, pp. 32-46.

Majumder et al., "Bilateral Lingual Nerve Injury Following the Use of the Laryngeal Mask Airway," Anaesthesia, 1998, vol. 53, pp. 184-186.

Martin, Todd, "Patentability of Methods of Medical Treatment: A Comparative Study," Jun. 2000, pp. 381-423.

Merriam Webster's Collegiate Dictionary, 10th ed., 1997, pp. 254 & 1029, definirtions of Convex & Saddle.

Miller, "A Pressure Regulator for the Cuff of a Tracheal Tube," Anaesthesia, 1992, vol. 47, pp. 594-596.

Muthuswamy et al., "The Use of Fuzzy Integrals and Bispectral Analysis of the Electroencephalogram to Predict Movement under Anesthesia," IEEE Transactions on Biomedical Engineering, 1999, vol. 46(3), pp. 290-299.

Nagai, "Unilateral Hypoglossal Nerve Paralysis Following the Use of the Laryngeal Mask Airway," Anaesthesia, 1994, vol. 49, pp. 603-604.

Neurometric Assessment of Adequacy of Intraoperative Anesthetic, Mar. 1999, 3 pages, www.pnl.gov/medical/info/neuro.htm.

Observations by Third Party Concerning European Patent Application No. 99 947 765.6-2318, European Patent Office, Munich, Germany, Jan. 18, 2005, (3 pages).

Patel et al., "Tracheal Tube Cuff Pressure," Anaesthesia, 1984, vol. 39, pp. 862-864.

Pennant, "Comparison of the Endotracheal Tube and Laryngeal Mask in Airway Managemet by Paramedical Personnel," Anesth. Analg., 1992, vol. 74, pp. 531-534.

Pinnin et al., "Long-Term Tracheal Intubation Practice in the United Kingdom," Anaesthesia, 1983, vol. 38, pp. 791-795.

Raeder et al. "Tracheal Tube Cuff Pressures," Anaesthesia, 1985, vol. 40, pp. 444-447.

Response to Complaint Matter No. 4b 0 440-05, In the Matter of: LMA Deutschland GmbH versus Ambu (Deutschland) GmbH, Feb. 10, 2006, pp. 1-47.

Rieger et al., Anesthesiology, vol. 87, No. 1, Jul. 1997.

Seegobin et al., "Endotracheal Cuff Pressure and Tracheal Mucosal Blood Flow: Endoscopic Study of Effects of Four Large Volume Cuffs," British Medical Journal, 1984, vol. 288.

Willis et al., "Tracheal Tube Cuff Pressure," Anaesthesia, 1988, vol. 43, pp. 312-314.

Worthington, et al., "Proceedings of the Anaesthetic Research Society," Br. J. Anaesthesia, 1995, vol. 75, pp. 228P-229P.

Wynn et al., "Tongue Cyanosis After Laryngeal Mask Airway Insertion," Anesthesiology, 1994, vol. 80(6), pp. 1403.

Request for Inter Partes Reexamination Pursuant to 37 CFR 1.913 filed with the United States Patent and Trademark Office by Third Party Requester, Jan. 3, 2007, pp. 1-16 and Exhibits 1-16.

* cited by examiner

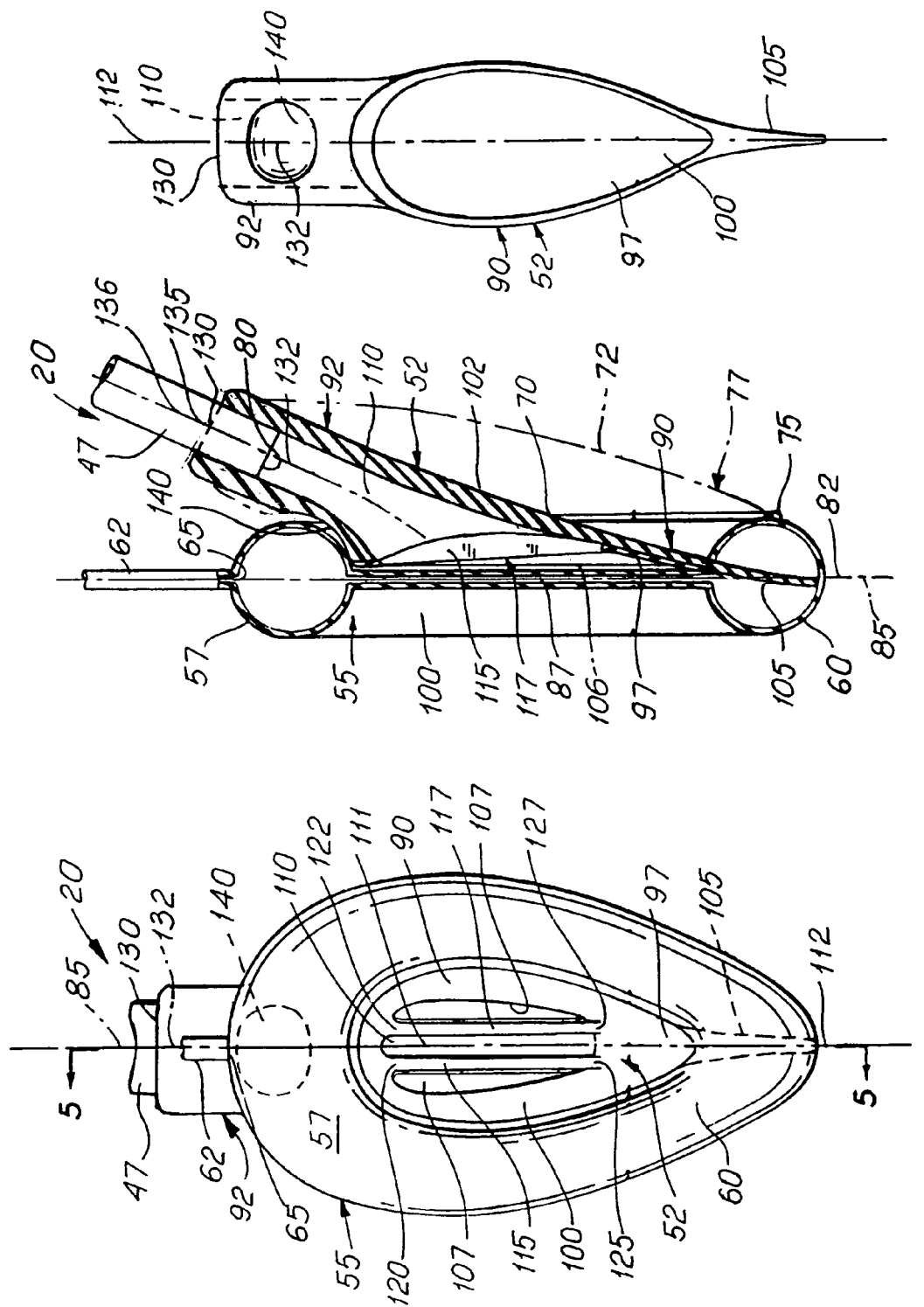

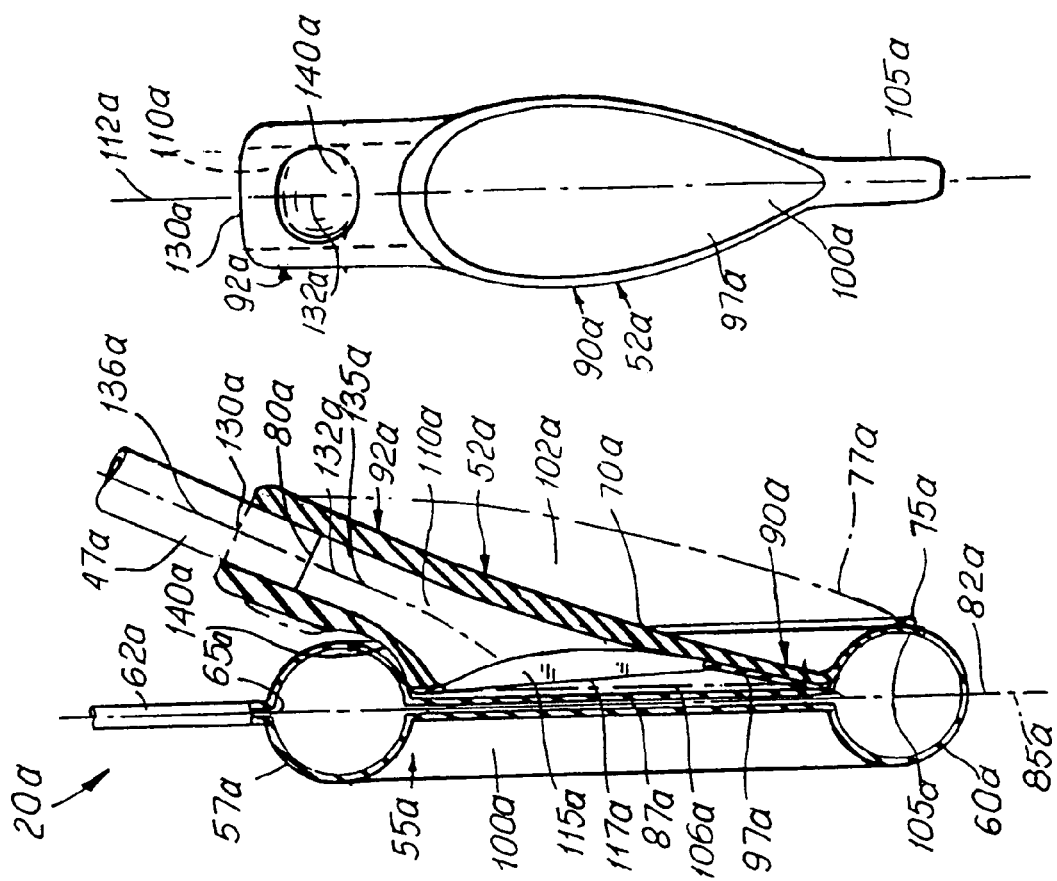
FIG. 11
FIG. 10
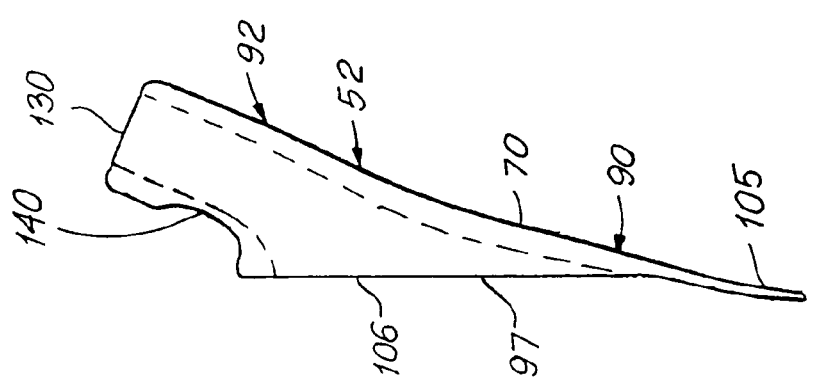
FIG. 9

LARYNGEAL MASK AIRWAY DEVICE

CROSS-REFERENCE SECTION

This application is a divisional application of currently U.S. patent application Ser. No. 09/412,954, filed Oct. 5, 1999.

BACKGROUND OF THE INVENTION

This invention relates to laryngeal mask airway devices (LMA-devices) which are artificial airway devices permitting spontaneous or artificial ventilation of the lungs of a patient.

LMA-devices are described in UK Patents Nos. 2,111,394 and 2,205,499. Such devices have become accepted items of equipment for rapidly and reliably establishing an unobstructed airway in a patient in emergency situations and in the administration of anaesthetic gases, and have found use in most countries of the world.

The insertion of such a LMA-device into the throat of the patient is, in the great majority of cases an entirely straightforward procedure which can be carried out successfully following readily understandable training. FIG. 1 illustrates a preferable situation for the insertion of an LMA-device into a patient's throat. The inflatable cuff surrounding the bowl of the mask is fully deflated and correctly oriented and aligned for passage through the back of the mouth and into the throat. The semi-rigid bowl of the mask is supported by the anesthetist's hand grasping the flexible airway tube adjacent its junction with the mask in order to gently urge the mask into the patient's throat.

Circumstances do, however, occasionally arise during insertion leading to undesirable positioning of the device and/or undesirable forces being applied to the device and/or to the patient. One of the most common of such circumstances is that the leading end of the device, i.e., the distal end of the fully deflated inflatable cuff formation, becomes folded over on itself presenting the more rigid distal end of the mask to catch the inside the throat and subject the patient to undesirable forces. Alternatively, or additionally, the folded over distal end of the cuff will obstruct correct and full inflation of the cuff thereby obstructing the creation of a full seal around the patient's laryngeal inlet and hence obstructing formation of a full enclosed airway to the patient's lungs. This, in turn, may result in anesthetic gases passing unnecessarily into the patient's oesophagus and in any matter regurgitated through the oesophagus entering the larynx and soiling the patient's trachea and lungs.

SUMMARY OF THE INVENTION

The present invention seeks to eliminate the disadvantages associated with such undesirable insertion by minimizing the risk of the deflated cuff formation becoming folding over on itself during the insertion procedure. This is achieved by incorporating into the cuff at its distal end a reinforcing rib which serves to stiffen the leading end of the LMA-device during the course of the procedure for its insertion.

In accordance with the invention, there is provided a laryngeal mask airway device comprising a flexible airway tube and a mask attached to one end of the airway tube, the mask having a generally elliptical periphery provided with an inflatable cuff which surrounds the hollow interior of the mask into which the airway tube opens, the device including a reinforcing rib incorporated into the distal end of the inflatable cuff.

In a preferred aspect, the mask structure or backplate which is of a more rigid material than that of the soft and inflatable cuff formation has its back extended to the distal end of the cuff, in order to form the reinforcing rib.

The LMA-device of the invention incorporating such a reinforcing rib has a number of advantages over and above that for which it was specifically devised. Thus, not only does the reinforcing rib largely eliminate the likelihood of the distal end of the deflated cuff formation folding over on itself during insertion of the LMA-device into the patient's throat, but also the cuff is easier to deflate preferably since the reinforcing rib will urge the deflating cuff into the desired orientation. Since the cuff in its deflated state may adopt an upturned or down turned orientation, the reinforcing rib will urge the deflated cuff into the down turned position desirable for insertion into the patient. Further, in addition to the rib being stiffer than the deflated cuff, it will preferably also be more compliant than the material of the bowl of the mask and the stiffness gradient formed by the rib and the mask will assist in the insertion of the device and substantially reduce the likelihood of any hard or angular edges of the bowl of the mask being presented which may subject the patient's throat to undesirable forces. Additionally, the rib will substantially reduce the promontory previously formed by the distal end of the mask structure, rendering the LMA-device substantially self-inserting when it is properly deflated.

As shown in FIG. 1, insertion of the LMA-device requires use of the index finger to ensure correct placement of the LMA-device in the base of the throat. However, the index finger may slip from its intended position on the airway tube at the proximal end of the inflatable cuff, due to the presence of slippery secretions in the patient's mouth and/or the application of lubricant to assist smooth passage of the LMA-device.

In accordance with a preferred aspect of the invention, an indentation is provided on the airway tube or backplate at the intended location of finger contact to assist in locating and stabilizing the finger and to reduce the possibility of finger slippage. The indentation is situation on the surface of the airway tube adjacent its junction with the tube-joint, or on the tube-joint itself, and beneath the cuff formation surrounding the backplate. The airway tube usually has a thicker wall at this point, i.e., near the distal end of the airway tube, to form a smooth joint with the tube-joint, and the extra thickness enables the indentation to be accommodated without weakening the airway tube at this location. The tube-joint may also have a thicker wall at this point. Indeed, the indentation serves the additional useful purpose of improving the flexibility of the airway tube or tube-joint at this point. The indentation serves not only to prevent sideways slippage of the finger from the airway tube or tube-joint, but also to minimize the possibility of forward slippage and undesirable contact between the finger and the inflatable cuff, for example by the fingernail.

An additional difficulty which may occur during attempts to insert the LMA-device is that the patient's epiglottis (which protects the entrance to the glottis or larynx) may be pushed downwards or anteriorly as the LMA-device is inserted fully into the throat. Indeed, this occurs in about 40% of cases and can sometimes obstruct breathing. A conventional LMA-device has the interior of the mask which in use surrounds the glottis, communicating with the interior of the airway tube through an aperture which is traversed by two bars, known as mask aperture bars (MABs). The MABs function as a ramp up which the epiglottis slides as the mask is inserted and are intended to hold the epiglottis away from the mask floor when the LMA-device is in its correct operating location. Additionally, the MABs serve to prevent the epiglottis from obstructing the narrow entrance of the airway tube. Generally, the MABs successfully perform this function but occasionally obstruction may occur if the epiglottis is down folded, e.g., anteriorly, or if the mask is not sufficiently advanced into place.

In accordance with a preferred aspect of the invention, the aperture by which the interior of the airway tube opens into the mask is elongated and the MABs are extended to traverse the length of that aperture. By elongating the aperture to half the bowl of the mask, the range of positions of the LMA-device compatible with a clear airway is greatly increased and the angle of ramp up which the epiglottis must slide is reduced, both of which make the epiglottis less likely to be down-folded during insertion of the LMA-device.

BRIEF DESCRIPTION OF THE DRAWINGS

In the drawings:

FIG. 4 is an anterior plan view of the device of FIG. 1 removed from the patient, the proximal portions of the airway and inflation tubes being broken away, the indentation on the backplate being shown as hidden;

FIG. 5 is a cross-sectional view of the device in the plane indicated by line 5-5 of FIG. 4, the proximal portions of the airway and inflation tubes being broken away;

FIG. 6 is an anterior plan view of the backplate removed from the device shown in FIG. 5;

FIG. 9 is a lateral view of the backplate removed from the device shown in FIG. 5;

FIG. 10 is a cross-sectional view of a second embodiment of the device of FIG. 1 removed from the patient, the device being shown in the plane of FIG. 5, the proximal portions of the airway and inflation tubes being broken away; and FIG. 11 is an anterior plan view of the backplate removed from the device shown in FIG. 10.

Corresponding reference characters indicate corresponding parts throughout the several views of the drawings.

DETAILED DESCRIPTION OF THE INVENTION

As used herein, the anatomical terms "anterior" and "posterior", with respect to the human body, refer to locations nearer to the front of and to the back of the body, respectively, relative to other locations. The term "anterior-posterior (A-P)" refers to a direction, orientation or the like pointing either anteriorly or posteriorly. The anatomical terms "proximal" and "distal", with respect to applying an instrument to the human body, refer to locations nearer to the operator and to the inside of the body, respectively. Alternatively, "distal", as opposed to "proximal", means further away from a given point; in this case, "distal" is used to refer to positions on the LMA-device 20 or in the body relative to the extreme outer or connector end of the LMA-device. "Proximal" is the opposite of "distal". The term "lateral" refers to a location to the right or left sides of the body, relative to other locations. Alternatively, "lateral" means to one or other side of the mid-line, with respect to the major axis of the body, or to a device lying in the body's major axis. The term "bilateral" refers to locations both to the left and right of the body, relative to the sagittal plane. The term "sagittal" or "sagittally" refers to a vertical longitudinal plane through the center or midline of the body that divides a bilaterally symmetrical body into right and left halves. The sagittal plane is the plane passing antero-posteriorly through the middle of the body in its major axis. The term "medial" means nearer to the mid-line.

Figure 1:
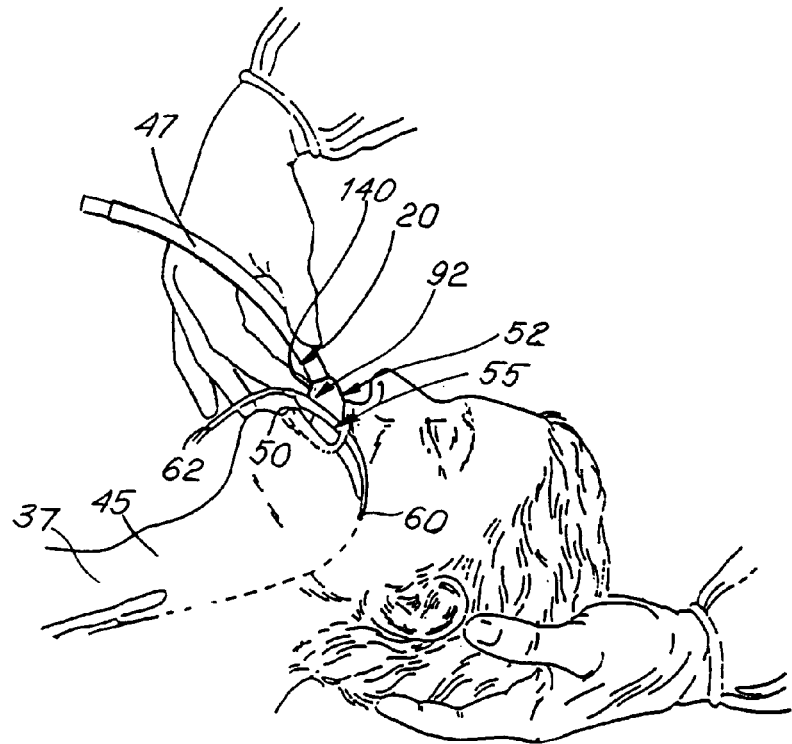
FIG. 1 is a perspective view of the laryngeal-mask airway device of the present invention being inserted into the throat of a patient.
Figure 2:
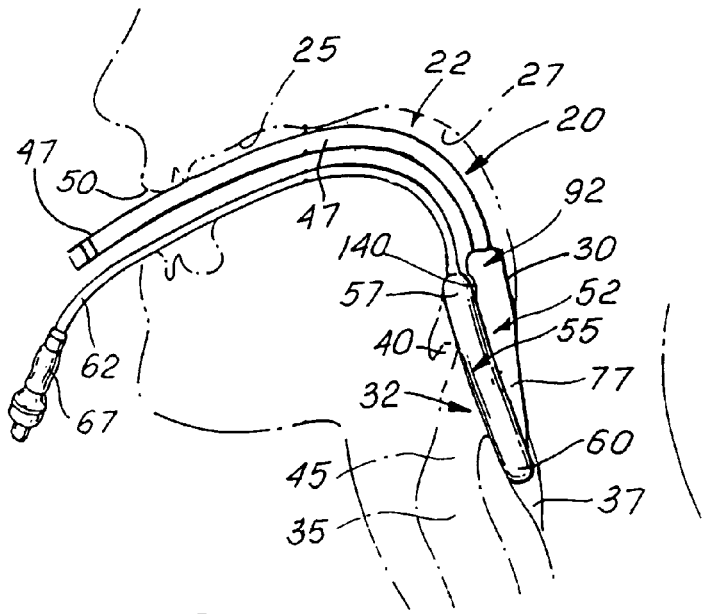
FIG. 2 is a side view of the device of FIG. 1 inserted into sealed engagement with the tissue surrounding the laryngeal inlet of the patient.

A laryngeal-mask airway device (LMA-device) of the present invention, is designated generally by the reference numeral 20 in FIGS. 1 and 2. The LMA-device 20, in a deflated condition, is inserted into the throat 22 the upper surface of which is bounded by hard and soft palates 25, 27. The LMA-device 20 is lodged in the pharynx 30 of the throat 22 at the base of the hypo-pharynx 32 where the throat divides into the trachea 35 (i.e., windpipe) and oesophagus 37. A lower portion of the LMA-device 20 reaches to the base of the hypo-pharynx 32. After the LMA-device 20 is so lodged in the pharynx 30 such that the lower portion of the LMA-device reaches the base of the hypo-pharynx 32, the LMA-device is inflated. Disposed in the junction between the throat 22 and trachea 35 is the flexible epiglottis 40 (i.e., a lid-shaped structure) which forms the upper border of the larynx, entry through which is provided by the laryngeal inlet 45.

Figure 3:
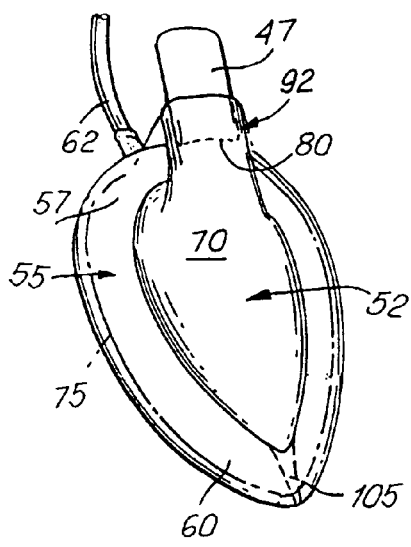
FIG. 3 is a posterior perspective view of the device of FIG. 1 removed from the patient, the proximal portions of the airway and inflation tubes being broken away, the back-cushion being cut-away.

Referring to FIGS. 1 and 2, and more particularly to FIG. 3, the laryngeal-mask airway device (LMA-device) 20 is shown comprising an airway tube 47, installed through the mouth 50 of a patient. The LMA-device 20 further comprises a backplate 52 having an airway port 55 through which the airway tube 47 can establish a free externally accessible ventilation passage, via the patient's mouth 50 and throat 22, and past the epiglottis 40 to the larynx. The backplate 52 is preferably of an elastomer such as silicone rubber and relatively stiff, for example, of 80 Shore durometer.

As further shown in FIGS. 3 and 4, the backplate 52 is surrounded by a main-cuff 55 comprising an inflatable ring which, when inflated, has the shape of a torus generated by an asymmetrical oval or ellipse having a wider proximal region 57 and narrower distal region 60. The main-cuff 55 is circumferentially united to the backplate 52 in essentially a single plane.

An externally accessible cuff-tube 62 and cuff-port 65 on the main-cuff 55 are the means of supplying air to the main-cuff and of extracting air from (and therefore collapsing) the main-cuff for purposes of insertion in or removal from the patient. The check-valve 67 is disposed in the cuff-tube 62 for holding a given inflation or holding a given deflation of the main-cuff 55.

In the installed position of FIGS. 1 and 2, the projecting but blunted distal region 60 of the main-cuff 55 is shaped to conform with the base of the hypo-pharynx 32 where it has established limited entry into the upper sphincteral region of the oesophagus 37. The pharyngeal-side 70 of the backplate 52 is covered by a thin flexible panel 72, as shown in FIGS. 3 and 5, which is peripherally bonded to a margin 75 on the posterior surface of the main-cuff 55, to define an inflatable back-cushion 77 which assures referencing to the posterior wall of the pharynx 30 and thus is able to load the inflated main-cuff 55 forward for enhanced effectiveness of sealing engagement to the tissues surrounding the laryngeal inlet 45. The inflated main-cuff 55, thus-engaged to the laryngeal inlet 45, orients a portion of the airway tube 47 including the distal-end 80 at an acute angle to a mid-line major plane 82 of the main-cuff 55 and in substantial alignment with the axis of the laryngeal inlet 45, for direct airway communication only with the larynx.

The major plane 82 is a plane containing the major axis 85 of the main-cuff 55 extending between proximal and distal regions 57, 60. The major plane 82 is disposed between, and parallel to, the anterior and posterior surfaces of the main-cuff 55. Additionally, the major plane 82 is equidistant from the anterior and posterior surfaces of the main-cuff 55.

More specifically, and with particular reference to FIG. 5, the toroidal-shaped main-cuff 55 is formed by first moulding it in an intermediate stage having opposing edges, each of which has an elliptical shape. The opposing edges of the main-cuff 55, when in generally edge-to-edge relation, are welded together to form an internal seam 87, as shown in FIG. 5. The seam 87 defines an oval contained in a plane which is parallel to the major plane 82, corresponding to the internal surface of the main-cuff 55.

As used herein, the term "welding" describes the bonding together of two components having the same or similar chemical compositions, either by adhesive having the same or similar chemical composition as the components, or by high pressure or temperature fusion, or a combination of any of them.

The back-cushion 77, or auxiliary rear cushion, overlies the posterior surface of the backplate 52, as shown in FIGS. 3 and 5. Construction of the back-cushion 77 is described in U.S. Pat. No. 5,355,879, the contents of which are hereby incorporated by reference herein.

Inflation-air supply to the back-cushion 77 may be via one or more ports in the main-cuff 55 which provide communication between the interiors of the main-cuff and back-cushion so that both are inflated and deflated together. Alternatively, inflation-air supply to the back-cushion 77 may be via a separate inflating means, such as an inflation tube (not shown), similar to cuff-tube 62, may be provided for the back-cushion so that the back-cushion 77 and main-cuff 55 are separately and independently inflatable and deflatable.

If the main-cuff 55 and back-cushion 77 are inflated and deflated together, communication between the main-cuff and back-cushion may be facilitated by a separate tube (not shown), preferably with multiple perforations along its length, contained within the main-cuff in communication with the cuff-port 65 such that each perforation communicates with a port between the interiors of the main-cuff and back-cushion 77. Such a separate tube preserves a flowpath between the cuff-port 65 and back-cushion 77 if the main-cuff 55 is completely collapsed from deflation, thereby providing for further deflation of the back-cushion 77 via the cuff-port 65. Alternatively, a channel (not shown) may be formed on the inner surface of the main-cuff 55 between the opening of the cuff-tube 62 into the main-cuff and at least one of the one or more ports between the interiors of the main-cuff and back-cushion 77. Such a channel preserves a flowpath between the cuff-tube 62 and back-cushion 77 if the main-cuff 55 is completely collapsed from deflation.

The backplate 52 has a one-piece, integral spoon-shape including a bowl 90 and an external tube-joint 92 oriented proximally relative to the bowl, as shown in FIGS. 5 and 6.

Opposite proximal sides of the bowl 90 are defined by a convex pharyngeal-side 95 and concave laryngeal-side 97. The bowl 90 is relatively shallow in the anterior-posterior direction. The bowl 90 also has an elongate integral reinforcing distal rib 105.

The proximal portion of the bowl 90 sandwiched between the pharyngeal- and laryngeal-sides 95, 97 abuts the posterior surface of the seam 87, as shown in FIG. 5, to attach the backplate 52 to the main-cuff 55. More specifically, the periphery of the proximal portion of the bowl 90 sandwiched between the pharyngeal- and laryngeal-sides 95, 97 is hermetically bonded to the inner periphery of the main-cuff 55 to establish separation between the laryngeal-chamber region 100 and pharyngeal region 102. The seam 87 may also be inserted into a corresponding groove in the bowl 90. Alternatively, the backplate 52 and main-cuff 55 may be extruded as a single, unitary piece. The periphery of the bowl 90 which abuts the inner periphery of the main-cuff 55 defines a bowl plane 106 which is parallel to the major plane 82 of the main-cuff 55.

When the backplate 52 is attached to the main-cuff 55, the distal rib 105 pierces the proximal surface of the distal region 60. The edges of the main-cuff 55 in the distal region 60 surrounding the distal rib 105 are hermetically sealed to it such that the enclosure of the main-cuff is defined in part by the distal rib. The distal rib 105 extends through the interior of the main-cuff 55 to the distal surface of the distal region 60.

The bowl 90 has a longitudinally elongated airway aperture 107 into which opens a backplate passage 110 extending through the tube-joint 92. The airway aperture 107 has a major axis 111 which is contained in the sagittal plane 112.

Two mask aperture bars (MABs) 115, 117 extend longitudinally and anteriorly of the airway aperture 107, as shown in FIG. 4. The MABs 115, 117 are disposed on opposite sides of the sagittal plane 112 and symmetrical relative to the plane. The MABs 115, 117 each have a proximal end 120, 122 abutting the laryngeal-side 97 of the bowl 90 proximally of the airway aperture 107. Additionally, the MABs 115, 117 each have a distal end 125, 127, abutting the laryngeal-side 97 of the bowl 90 distally of the airway aperture.

The MABs 115, 117 may be defined by a portion of a continuous layer of elastomer, integral with the main-cuff 55, which overlies the laryngeal-side 97. The elastomer layer has an opening the periphery of which is outward of the airway aperture 107. The opening is longitudinally traversed by the MABs 115, 117.

Figure 8:
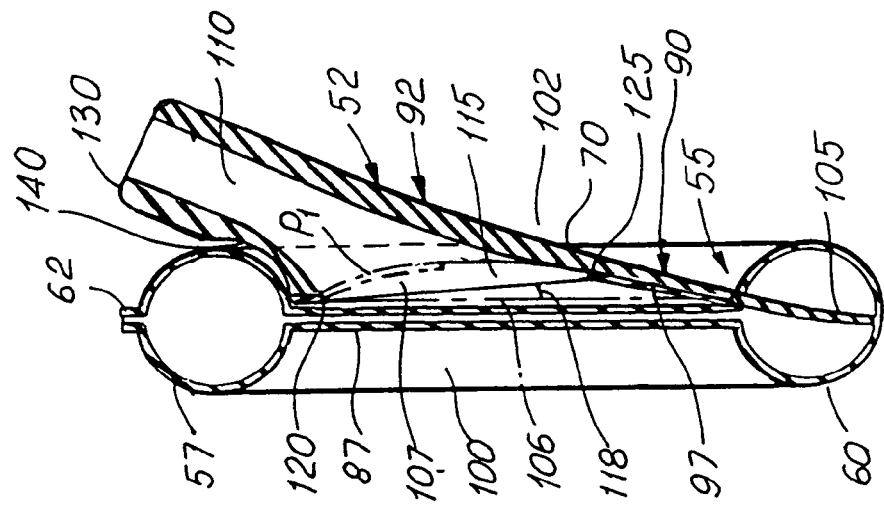
FIG. 8 is a cross-sectional view of the device in the plane of FIG. 5 showing one of the mask aperture bars of the present invention, in solid lines, and one of the mask aperture bars of a prior laryngeal-mask airway device, in broken lines, the proximal portions of the airway and inflation tubes being broken away.

The distal ends 125, 127 of the MABs 115, 117 are joined to the bowl 90 generally near the longitudinal mid-point of the laryngeal-side 97, or distally of it. This results in each MAB 115, 117 forming an angle 118 with the bowl plane 106 which is less than the corresponding angle between the MAB P1 of a prior LMA-device, as shown in FIG. 8. The relative shallowness of the bowl 90 in the anterior-posterior direction further results in the angle 118 being more acute. A preferred angular displacement of the angle 118 is between 7 and 12 degrees, and may preferably be 9 degrees.

The elongate tube-joint 92 is formed on the pharyngeal-side 95 and extends posteriorly and proximally relative to the bowl 90. The tube-joint 92 has a proximal end 130 from which the backplate passage 110 extends to the airway aperture 107 in the laryngeal-side 97. The backplate passage 110 has a longitudinal central axis 132 contained in the sagittal plane 112. At the proximal end 130, the backplate passage 110 has an elliptical cross section with a major axis 135 oriented in perpendicular relation to the sagittal plane 112. The major axis 135 is therefore transverse to the major axis 111 of the airway aperture 107. This differing orientation of the major axes 111, 132 of the backplate passage 110 is accomplished by a smooth transition in the cross-sectional shape of the backplate passage along its length.

Figure 7:
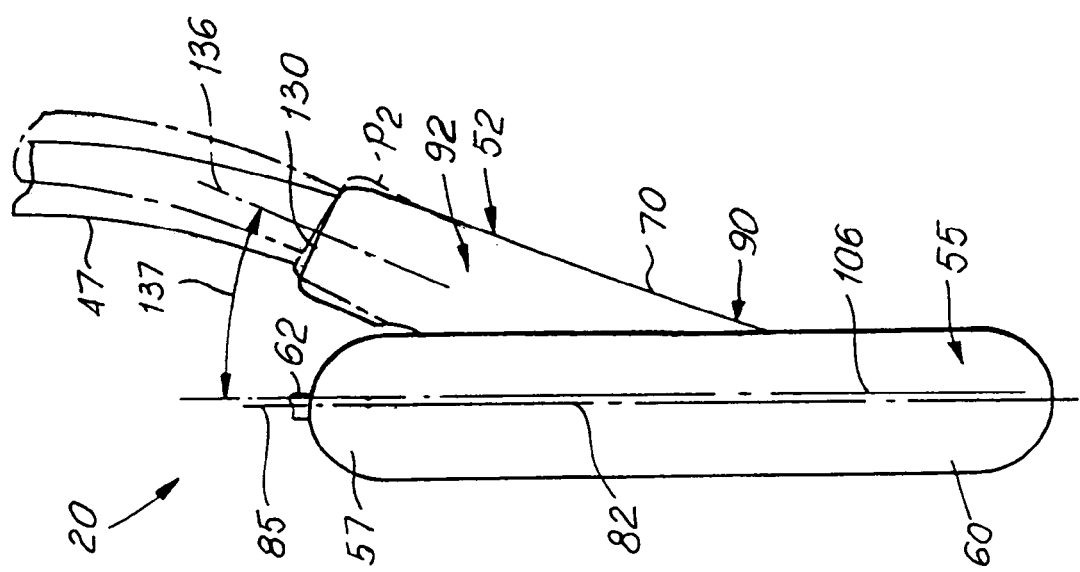
FIG. 7 is a schematic view of the device in the plane of FIG. 5 showing the present invention, in solid lines, and an airway tube and adjoining portion of the backplate of a prior laryngeal-mask airway device, in broken lines, the proximal portions of the airway and inflation tubes being broken away.

The tube-joint 92, and the central axis 132 of the backplate passage 110 are inclined posteriorly in the sagittal plane 112 relative to a plane containing the periphery of the bowl 90. In the embodiment shown in FIG. 5, the inclination of the tube-joint 92 may be defined by a tube-joint axis 136 which is perpendicular to the cross-section of the proximal end 130 and which coincides with the central axis 132 at its intersection with the cross-section of the proximal end 130. The inclination of the tube-joint 92 may be further defined by an angle 137 between the tube-joint axis 136 and bowl plane 106. A preferred angular displacement of the angle 137 is between 5 and 10 degrees, and may preferably be 7 degrees. The inclination of the tube-joint 92, defined by the angle 137, is less than the corresponding angle defined by the inclination of a tube-joint P2 of a prior-LMA, as shown in FIG. 7.

The anterior surface of the tube-joint 92 has an indentation 140, as shown in FIGS. 4, 5, 6 and 9. As shown in FIG. 5, the indentation 140 is in the thick wall region of the tube-joint 92 resulting in the advantage of increasing the flexibility of the tube-joint. The indentation 140 may be occupied by the main-cuff 55 when the main-cuff is inflated. The indentation 140 may also be formed closer to the proximal end 130, such as is shown in FIG. 1. Alternatively, the proximal portion of the indentation 140 may also be formed across the boundary between the tube-joint 92 and airway tube 47 such that portions of the indentation are both the airway tube and tube-joint. Also, the entire indentation 140 may be formed in the airway tube 47 adjacent to its connection to the tube-joint 92.

The backplate 52, main-cuff 55 and back-cushion 77 of LMA-devices 20 are generally manufactured by molding techniques from suitably soft and compliant rubber materials. The backplate 52 and inflatable main-cuff 55 may be formed as a one piece molding by molds and molding techniques such as are described, for example, in U.S. Pat. No. 5,305,743, the contents of which are hereby incorporated herein. The backplate 52 is formed to have a greater thickness than the walls of the main-cuff 55 to provide the LMA-device 20 with a degree of rigidity while still allowing it to have an overall soft and flexible nature. The main-cuff 55 has a thin-walled construction and the reinforcing distal rib 105 has an intermediate thickness and compliancy.

As shown in FIGS. 4 and 5, the portion of the airway tube 47 containing the distal end 80 is supported in the backplate passage 110 of the tube-joint 92 in communication with the airway aperture 107 in the laryngeal-side 97. Such communication provides a flowpath between the airway tube 47 and laryngeal-chamber region 100. The airway tube 47 is connected to the tube-joint 92 by welding using an adhesive or, alternatively, connected by high-pressure or temperature fusion.

FIG. 10 shows a second embodiment of the backplate 52a. Parts in FIG. 10 having corresponding parts in FIGS. 5 and 6 have the same reference numeral with the addition of suffix a. The backplate 52a is similar to the backplate 52 illustrated in FIGS. 5 and 6 except that the distal rib 105a of the backplate 52a is applied to the posterior surface of the distal region 60a of the main-cuff 55a, as shown in FIG. 10. The distal rib 105a has a concave anterior surface corresponding to the adjoining convex posterior surface of the distal region 60a thereby limiting the radial clearance between the distal region and end 60a, 105a. The distal rib 105a does not pierce the posterior surface of the distal region 60a, in contrast to the embodiment shown in FIG. 5, and is therefore separated from the interior of the main-cuff 55a. The distal rib 105a may be effectively constituted by a thickening of the posterior wall of the distal region 60a of the inflatable main-cuff 55a and, as shown, forms a distal extension of the bowl 90a of the backplate 52a. The distal rib 105a has a downturned profile by being incorporated into the posterior surface of the main-cuff 55a. The distal end of the distal rib 105a is spatulate.

Insertion of the LMA-device 20 into the patient's throat 22 is illustrated in FIG. 1, and is done preferably with the patient in a supine orientation and the head 142 of the patient tilted backwards and supported from below by the left hand 145 of the anaesthetist. The right index finger 147 and thumb 150 of the anesthetist gently grasps the flexible airway tube 47 of the LMA-device 20. The right index finger 147 is located at the junction of the airway tube 47 and the main-cuff 55 to gently urge the LMA-device 29 with its down-turned deflated main-cuff into the patient's throat 22. As shown in FIG. 1, the indentation 140 provides a locator for the right index finger 147 of the anaesthetist during insertion of the LMA-device 20 into the throat 22 of the patient. When the LMA-device 20 is properly positioned across the patient's laryngeal inlet 45, the main-cuff 55 is gently inflated through cuff tube 62 to form an airway seal around the laryngeal inlet and establish a closed airway to the patient's lungs. The LMA-device 20 so positioned, with the main-cuff 55 fully inflated, is shown in FIG. 2. The thin-walled construction of the main-cuff 55 enables it, when inflated, to present to the tissues surrounding the laryngeal inlet 45 a softly compliant sealing surface.

As shown in FIG. 1, the distal region 60 of the fully deflated main-cuff 55 is the leading end of the LMA-device 20 when inserting the LMA-device into the patient's throat 22. Careful insertion of the LMA-device 20 into the patient's throat 22 is required to prevent the distal region 60 from folding over onto itself because the distal region is formed of a soft and flexible material which facilitates such folding over. Such folding over is obstructed by the reinforcing distal rib 105 within the distal region 60 of the inflatable main-cuff 55. The intermediate thickness and compliancy of the reinforcing distal rib 105 allows it to follow the contours of the posterior surface of the inflated main-cuff 55, thereby to urge the deflated main-cuff into the desired downturned orientation and to enable the LMA-device 20 present a distal end to the tissues of the throat 22 which is sufficiently pliable to avoid undesirable contact with the throat during its insertion but sufficiently rigid to prevent it from being readily folded over on itself during such a procedure. As shown in FIGS. 3 and 4, the distal rib 105 is not readily visible when the main-cuff 55 is either deflated or inflated since it is contained within the distal region 60.

In the embodiment shown in FIG. 10, the downturned profile the distal rib 105a helps to facilitate adoption by the main-cuff 55a of the desired downturned orientation when it is fully deflated. The distal rib 105a may not be readily visible because it may appear to blend in with the posterior wall of the distal region 60. The spatulate of the distal portion of the distal rib 105a does not present any sharp edges or corners to the throat 22 the patient during insertion of the LMA-device 20 which is desirable as striking of the throat 22 by sharp edges or corners is normally to be avoided.

The acute angle 118 between the MABs 115, 117 and the bowl plane 106 results in the MABs presenting a substantially less gradient to the patient's epiglottis 40 than the MABs P1 of a prior-LMA, as shown in FIG. 8. The MABs 115, 117 provide a ramp up which the epiglottis 40 slides when the backplate 52 and the attached main-cuff 55 enter the pharynx 30. If the MABs are sufficiently posterior of the epiglottis 40, e.g., MAB P1, such sliding contact may result in the proximal end of the epiglottis 40 folding over posteriorly such that it becomes sandwiched between the base of the epiglottis and the MABs possibly obstructing the airway aperture 107. The likelihood of such posterior folding over of the epiglottis 40 is substantially reduced by the MABs 115, 117 because the A-P clearance between the MABs 115, 117 and laryngeal-side 97 is increased thereby anteriorly propping the epiglottis to limit further anterior displacement necessary to accommodate the posterior folding. Further reduction in the likelihood of an obstruction is provided by the increased A-P clearance between the MABs 115, 117 and laryngeal-side 97, which in turn provides increased A-P clearance between the epiglottis 40 and airway aperture 107 contained in the laryngeal-side.

When the main-cuff 55 and backplate 52 are installed in the pharynx 30 such that main-cuff is sealed against the tissues surrounding the patient's laryngeal inlet 45, the reduced angle 137 between the tube-joint axis 136 and bowl plane 106, relative to the corresponding force resulting from tube-joint P2, reduces the force exerted by the tube-joint 92 and airway tube 47 against the posterior surface of the throat 22. Any force against the tissues of the throat 22 should normally be limited.

The reduction in the force exerted by the tube-joint 92 and airway tube 47 against the posterior surface of the throat 22 may result in a reduction in the reaction force of the main-cuff 55 against the tissues surrounding the patient's laryngeal inlet 45 which, in turn, may reduce the tightness of the seal between the main-cuff and tissues. Any such reduction in the seal is compensated for the inflatable back-cushion 77 which gently urges the backplate 52 and main-cuff 55 anteriorly against the tissues surrounding the patient's laryngeal inlet 45 in order to reinforce the seal between the inflated main-cuff and the tissues.

Additionally, the inflatable back-cushion 77 presents a more softly compliant surface to the posterior surface of the patient's throat 22. Also, the back-cushion 77 enables the main-cuff 55 to be inflated at a lower pressure, i.e., typically 60 cm $H_2O$, as compared to the inflation pressure required of the main-cuff if the LMA-device 20 does not include a back-cushion 77. Reducing the inflation pressure of the main-cuff 55 enables a reduced wall thickness of the main-cuff.

While the invention has been described by reference to certain preferred embodiments, it should be understood that numerous changes could be made within the spirit and scope of the inventive concept described. Accordingly, it is intended that the invention not be limited to the disclosed embodiments, but that it have the full scope permitted by the language of the following claims.

What is claimed is:

1. A laryngeal-mask airway device comprising:
   (a) an inflatable cuff;
   (b) a backplate attached to the cuff establishing separation between a laryngeal-chamber region and a pharyngeal region, the cuff and backplate being insertable through a mouth of a patient to an inserted location within the patient, the laryngeal-chamber region being in communication with a laryngeal inlet of the patient when the cuff is inflated and when the cuff is at the inserted location, the backplate including a tube-joint disposed in the pharyngeal region, the device defining an indentation proximate the tube joint, the indentation being accessible by a finger of a person when the person is inserting the cuff and backplate through the mouth of the patient; and
   (c) an airway tube extending from the tube joint to a proximal end, the proximal end of the airway tube being disposed outside the patient's mouth when the cuff is at the inserted location, a continuous artificial airway extending from the proximal end of the airway tube to the laryngeal-chamber region;
   wherein the backplate further includes a passageway for communication between said pharyngeal and laryngeal-chamber regions, said backplate having a longitudinal distal rib for longitudinally supporting the distal region of said cuff, wherein the distal rib is narrower than the diameter of the passageway.

2. A device as set forth in claim 1, wherein the cuff includes a distal region and has an interior, wherein said distal rib extends into and through the interior of the distal region of said cuff.

3. A device as set forth in claim 2, wherein the cuff includes a distal tip wherein said distal rib has a distal tip which contacts the distal tip of said cuff.

4. A backplate for a laryngeal-mask airway device, said backplate comprising a bowl having a transversely concave laryngeal-side and a convex pharyngeal-side, said backplate being bonded to a periphery of a main-cuff establishing separation between a laryngeal-chamber region and a pharyngeal region,
   said backplate further comprising an external tube-joint, said tube-joint being formed on said pharyngeal-side and extending from said pharyngeal-side into said pharyngeal region, said tube-joint further including a passageway for communication between said pharyngeal and laryngeal-chamber regions, said device having an anterior outer surface defining an indentation proximate the tube joint, the indentation being accessible by a finger of a person when the person is inserting the device into a patient;
   wherein the backplate further includes a passageway for communication between said pharyngeal and laryngeal-chamber regions, said backplate having a longitudinal distal rib for longitudinally supporting the distal region of said cuff, wherein the distal rib is narrower than the diameter of the passageway.

5. A device as set forth in claim 4, wherein the cuff includes a distal region and has an interior, wherein said distal rib extends into and through the interior of the distal region of said cuff.

6. A device as set forth in claim 5, wherein the cuff includes a distal tip wherein said distal rib has a distal tip which contacts the distal tip of said cuff.

7. A laryngeal-mask airway device comprising:
   (a) an inflatable cuff;
   (b) a backplate attached to the cuff establishing separation between a laryngeal-chamber region and a pharyngeal region, the cuff and backplate being insertable through a mouth of a patient to an inserted location within the patient, the laryngeal-chamber region being in communication with a laryngeal inlet of the patient when the cuff is inflated and when the cuff is at the inserted location, the backplate including a tube-joint disposed in the pharyngeal region; and
   (c) an airway tube extending from the tube joint to a proximal end, the proximal end of the airway tube being disposed outside the patient's mouth when the cuff is at the inserted location, a continuous artificial airway extending from the proximal end of the airway tube to the laryngeal-chamber region, the tube joint and a portion of the airway tube proximal the tube joint having a laryngeal side and a pharyngeal side, the laryngeal side being closer to the patient's larynx than to the patient's pharynx when the device is at the inserted location, the laryngeal side of at least one of the tube joint and the portion of the airway tube defining an indentation, the indentation being accessible by a finger of a person when the person is inserting the cuff and backplate through the mouth of the patient.

8. The device of claim 7, wherein the indentation is formed in the tube-joint.

9. The device of claim 7, wherein the indentation is formed across a boundary between the tube joint and the airway tube.

10. A laryngeal mask airway device, comprising:
(a) an inflatable cuff, the cuff defining a central opening at least when inflated, the cuff being insertable through a mouth of a patient to an inserted location within the patient, the cuff surrounding a glottic opening of the patient when inflated and at the inserted location; and
(b) an airway structure extending from a proximal end to a distal end, the distal end of the airway structure being attached to the cuff, the airway structure defining an internal passage, a portion of the airway structure proximate the cuff having a laryngeal side and a pharyngeal side, the laryngeal side being closer to the patient's larynx than to the patient's pharynx when the device is at the inserted location, the laryngeal side of the airway structure defining an indentation proximate the cuff.

11. The device of claim 10, wherein said airway structure comprises:
a backplate comprising a bowl having a concave laryngeal-side and a convex pharyngeal-side, said backplate being bonded to said cuff establishing separation between a laryngeal-chamber region and a pharyngeal region, said backplate further comprising an external tube-joint, said tube-joint extending into said pharyngeal region, said tube-joint defining a passageway for communication between said pharyngeal and laryngeal-chamber regions; and
an airway tube extending from the tube joint to said proximal end, the proximal end of the airway tube being disposed outside the patients mouth when the cuff is at the inserted location, a continuous artificial airway extending from the proximal end of the airway tube to the laryngeal-chamber region.

12. The device of claim 11, wherein the indentation is formed in the tube-joint.

13. The device of claim 11, wherein the indentation is formed across a boundary between the tube joint and the airway tube.

14. The device of any one of claims 4 or 10, wherein the indentation projects inward from a surface substantially parallel to a central axis of the tube joint.

15. The device of any one of claims 4 or 11, wherein the indentation is formed in the airway tube.

* * * * *